US007846873B2

(12) United States Patent
Leeper

(10) Patent No.: US 7,846,873 B2
(45) Date of Patent: *Dec. 7, 2010

(54) METHOD TO USE A SYNERGISTIC COMPOSITION

(75) Inventor: John R. Leeper, Germantown, TN (US)

(73) Assignee: Riceco, LLC., Memphis, TN (US)

( * ) Notice: Subject to any disclaimer, the term of this patent is extended or adjusted under 35 U.S.C. 154(b) by 224 days.

This patent is subject to a terminal disclaimer.

(21) Appl. No.: 11/945,432

(22) Filed: Nov. 27, 2007

(65) Prior Publication Data

US 2009/0137392 A1 May 28, 2009

Related U.S. Application Data

(62) Division of application No. 11/232,191, filed on Sep. 21, 2005, now Pat. No. 7,560,416.

(51) Int. Cl.
  *A01N 63/00* (2006.01)
  *A01N 47/28* (2006.01)
  *A01N 47/40* (2006.01)
  *A01N 33/18* (2006.01)

(52) U.S. Cl. ................ 504/118; 504/141; 504/148; 514/741

(58) Field of Classification Search .......... 504/148, 504/118, 141; 514/741
See application file for complete search history.

(56) References Cited

U.S. PATENT DOCUMENTS

| | | | | |
|---|---|---|---|---|
| 4,497,646 | A | * | 2/1985 | Rubio ................ 504/339 |
| 5,650,373 | A | | 7/1997 | Ort |
| 5,869,425 | A | * | 2/1999 | Fisher et al. ........... 504/143 |
| 5,895,373 | A | | 4/1999 | Hirsch |
| 5,952,265 | A | | 9/1999 | Franz |
| 6,013,604 | A | | 1/2000 | Franz |
| 6,103,644 | A | | 8/2000 | Sheridan |
| 6,103,664 | A | | 8/2000 | Sievernich et al. |
| 6,281,168 | B1 | | 8/2001 | Shaner |
| 6,713,433 | B2 | | 3/2004 | Jimoh |
| 6,800,791 | B1 | | 10/2004 | Bailey |
| 6,831,014 | B2 | | 12/2004 | Tsuchiya |
| 6,844,294 | B2 | | 1/2005 | Auler et al. |
| 6,914,035 | B2 | | 7/2005 | Ziemer et al. |
| 7,560,416 | B2 | | 7/2009 | Leeper |
| 2003/0104941 | A1 | | 6/2003 | Auler et al. |

OTHER PUBLICATIONS

Scott, R.C., Post Flood Tank-Mix Combinations with Cyhalofop (Clincher) for Barnyardgrass (*Echinochloa crus-galli*) Control in Rice, 2002, AAES Research Series 504, pp. 165-168.*
Scherder, Eric, Antagonism of Cyhalofop Grass Activity by Halosulfuron, Triclopyr, and Propanil, Oct.-Dec. 2005, Weed Technology, vol. 19, pp. 934-941.*
Buehring, N., Interactions of Graminicides with Other Herbicides Applied to Rice (*Oryza sativa*), 2006, Weed Technology, vol. 20, pp. 215-220.*
Smith, Roy, Propanil and Mixtures with Propanil for Weed Control in Rice, Jul. 1965, Weeds, Abstract, pp. 1-2.*
U.S. Appl. No. 09/353,230, filed Sep. 5, 2002, Dr. Erwin Hacker, Hochheim.
Norsworthy J K et al., Agrichemical Interactions with Propanil on Propanil-resistant Barnyardgrass (*Echinochloa crus-galli*), Weed Technology, vol. 13, pp. 296-302.
Norsworthy J K et al., Chlorophyll Fluorescence Evaluation of Agrochemical Interactions with Propanil on Propanil-resistant Barnyardgrass, Weed Science, vol. 47 pp. 13-19.
Weed Control Programs, California Rice Production Workshop, Jan. 2004, Fischer, Albert, J. UCD, Hill James E. UCD.
New Rice Chemicals Are Tools, Not Programs, Commercial Agriculture Program, MU Delta Center, Rice, Oct. 16, 2002, Kendig, Andy, Extension Weed Specialist.
Corn and Grain Sorghum, Pest Management News, University of Arkansas, Division of Agriculture Cooperative Extension Service, May 30, 2002, Bernhardt, Entomologist RREC, et al.
Weed Doctor—Plan Ahead, Rice Journal, 2004, Smith, Ken.
Profile: Clincher, Regiment Herbicides, In Deltal Farm Press, May 9, 2003, Guy, C.B.
Herbicide Evaluation in Arkansas Rice, Arkansas Agricultural Experiment Station, Division of Agriculture, Apr. 2002, Talbert, Ron et al.
Ntanos, Dimitrios A., Barnyardgrass Control in Water-Seeded Rice with Cyhalofop-butyl, Week Technology, 2000, vol. 14: 383-388.
Ottis, B., Determination of Antagonism between Cyhalofop-butyl and other Rice Herbicides in Barnyardgrass, Journal of Agricultural Food Chemistry, 2005, 53, pp. 4064-4068.
The Facts about Tank mixing clincher SF herbicide with SuperWHAM! (propanil), www.rightforrice.com, May 2006.

* cited by examiner

*Primary Examiner*—Johann R Richter
*Assistant Examiner*—Andriae M Holt

(57) ABSTRACT

This invention relates to a method to use synergistic composition made of a herbicidally effective amount of a propanil-based product, such as Super Wham® and the at least one ACCase inhibitor herbicide such as Clincher® in an amount sufficient to facilitate the herbicidal activity of the propanil-based herbicide. It has been found that this synergistic composition, when applied to a field of rice, allows a reduction in the amount of herbicide needed, greater flexibility in timing of the application and broad spectrum of weed control.

5 Claims, No Drawings

METHOD TO USE A SYNERGISTIC COMPOSITION

FIELD OF THE INVENTION

This invention relates to a method to use synergistic herbicidal combinations, particularly, such combinations for use in controlling weeds in rice crops.

BACKGROUND OF THE INVENTION

Successful weed management is essential for economical rice production. In rice production, propanil-based products are applied at various leaf stages of the weeds to prevent the growth of weeds. Propanil is a photosystem II inhibitor that controls broadleaf, grass, and sedge weeds. Propanil based products, such as Super Wham® (propanil RiceCo, Inc., Memphis, Tenn.) have broad spectrum grass, broadleaf weed and sedge contact herbicidal activity, while at the same time being safe to rice. As a general rule of thumb, for every propanil susceptible grass leaf present, up to six leaves, one pound of propanil active ingredient per acre is needed to control the weed. Propanil resistant grasses are typically controlled by the addition of another grass herbicide to overcome resistance.

Another type of herbicides are the ACCase inhibitors such as: Cyhalofop sethoxydim, clethodim diclofop, fluazifop, fenoxaprop, quizalofop, clefoxydin and haloxyfop. ACCase inhibitor herbicides are known to be antagonistic when mixed with propanil (Kendig "New Rice Chemicals are Tools, Not Programs", MO Delta Center Rice Oct. 16, 2002). Poor weed control results have been observed with tank mixtures of ACCase inhibitor herbicides and propanil. G. Studebaker, University of Arkansas Pest Management News; (May 30, 2002); K. Smith. 'Plan Ahead. Do a good job upfront and know your herbicide capacity Rice Journal (2004); CB Guy, "Profile: Clincher (cyhalofop Dow Agro Science), Regiment herbicides (2003). (In Delta Parm Press.) In fact for many ACCase inhibitor herbicides, use with a propanil based herbicide are restricted in the rate and recommendation charts distributed by the manufactures.

SUMMARY OF THE INVENTION

When ACCase inhibitor herbicides are used at substantially lower than labeled rates in combination with propanil, the activity of the combination is superior to the components when used alone. Furthermore, there are no antagonistic effects in fact they are synergistic. This surprising effect will broaden the options for economic weed control for rice farmers due to allowing for a wider application window (greater flexibility in timing of application) and broader spectrum of weed control, such as control of Sprangletop, a grass not normally controlled by propanil. This invention relates to the use of synergistic composition to control weeds in a field of rice. The synergistic composition is made of as its active ingredient a herbicidal compound. The herbicidal compound includes an herbicidally effective amount of a propanil based herbicide and at least one ACCase inhibitor herbicide in an amount sufficient to facilitate the herbicidal activity of the propanil based herbicide. The synergistic composition can also include as an active ingredient an effective amount of an insecticide, fungicide, bactericide, acaracide, nematicide, plant growth regulator, fertilizer, or plant nutrients.

DETAILED DESCRIPTION OF THE INVENTION

This invention relates to the use of a synergistic composition to prevent the growth of weeds in a field of rice. More specifically, this invention involves a synergistic composition made of a combination of a herbicidally effective amount of a propanil based herbicide and at least one ACCase inhibitor herbicide in an amount sufficient to facilitate herbicidal activity of the propanil based herbicide. A herbicidally effective amount is an amount of herbicide necessary to arrest weed growth, when the herbicide is applied to the weeds. The amount of the ACCase inhibitor in this combination is an amount sufficient to facilitate herbicidal activity of the propanil based product. It has been found that this amount is substantially below the label rates for the use of ACCase inhibitor. In general, substantial below label rates are less than half the label rates. Presently, only Cyhalofop and Fenoxaprop are registered for use on rice in the USA and have rate and grass recommendations for rice. The other ACCase inhibitors are not labeled for use on a rice crop in the USA. The other ACCase inhibitors are not labeled for use on a rice crop; however, if only an amount sufficient to facilitate the activity of the propanil based herbicide are used, then heretofore unavailable ACCase inhibitor herbicides can function to control weeds in a rice crop in combination with a propanil based herbicide.

For example, Whip® 360 (fenoxaprop-p-ethyl Bayer Crop Science) shows a rate and grass recommendation chart for rice as follows:

TABLE 1

Rate and Grass Recommendation Chart for Rice

| | | Amount of Whip ® 360 (fenoxaprop-p-ethyl) Per Acre (pints) Relative to Stage of Annual Grass Weeds | | |
|---|---|---|---|---|
| Grass Species | | 1 to 3 leaf | 3 leaf to 2 tiller | >2 tiller or >10" |
| Sprangletop | (*Leptochioa* spp.) | 0.7 pt/A | 0.8 pt/A | 0.7 pt/A |
| Barnyardgrass, watergrass | (*Echinochioa crusgalli*) | | | to |
| Broadleaf signalgrass | (*Brachiaria platyphylla*) | | | 1.0 pt/A |
| Goosegrass | (*Eleusine indica*) | | | |
| Jungle rice | (*Echinochioa colonum*) | | | |
| Crabgrass | (*Digitaria* spp.) | | | |
| Johnsongrass (10"-15") | (*Sorghum halepense*) | | | |
| Giant foxtail | (*Setaria faberii*) | | | |
| Fall *panicum* | (*Panicum dichotomiflorum*) | | | |
| Red Rice | *Oryza sativa* | 0.7-1.0 pt/A | NOT RECOMMENDED | |

According to this invention, weeds are controlled in the presence of a rice crop by treating the crop, the weeds, or the locus of either or both, with a herbicidally effective amount of a synergistic combination of a propanil-based herbicide and at least one ACCase inhibitor herbicide in an amount sufficient to facilitate the herbicidal activity of the propanil based herbicide. In general, we have found that the synergy is demonstrated when the combination includes these two herbicides in a weight ratio respectively of from about 1 lb. propanil to about 0.0018 to 0.04 lbs. More specifically, in the preferred embodiment, wherein the at least ACCase inhibitor is cyhalofop the weight ratio of the herbicidal compound ranges, from about 1 lb. of said propanil based herbicide to about 0.009 to 0.04 lbs. of cyhalofop. Additionally, in an alternative preferred embodiment, wherein the at least ACCase inhibitor is fenoxaprop, the weight ratio of the herbicidal compound ranges, from about 1 lb. of the propanil based herbicide to 0.0018 to 0.007 lbs. of the fenoxaprop. However, it should be recognized that this weight ratio varies for each ACCase inhibitor, weed types, climate, soil and water conditions.

Additionally, another aspect of this invention is that lower amounts of a propanil based herbicide is required (for the same application) if the at least one ACCase inhibitor herbicide in an amount sufficient to facilitate the herbicide activity of the propanil based herbicide is added to the combination. It has been found that a combination of a propanil based herbicide, with the at least one ACCase inhibitor herbicide in an amount sufficient to facilitate herbicidal activity of the propanil based herbicide, results in on average 20% lower propanil, than if the same propanil based product is not used in combination the at least one ACCase inhibitor herbicide in an amount sufficient to facilitate herbicidal activity of the propanil based herbicide.

TABLE 2

| | Barnyard Grass | | | |
|---|---|---|---|---|
| | 2 to 3 Leaf | 3 to 4 Leaf | 4 to 5 Leaf | 5 to Tiller |
| Quantity Propanil Based Product (active) | 3 qt. (3 lb) | 4 qt. (4 lb) | 5 qt. (5 lb) | 6 qt. (6 lb) |
| Quantity Propanil Based Product + Clincher ® (cyhalofop) (active) | 2 qt. (2 lb) + 3 oz (0.056 lb) | 3 qt. (3 lb) + 4 oz. (0.074 lb) | 4 qt. (4 lb) + 4 oz. (0.074 lb) | 5 qt. (5 lb) + 5 oz. (0.093 lb) |

This combination produced synergistic or unexpected control of weeds in rice when applied at various times, and to rice planted in different ways. To control the weeds, the combination may be applied prior to planting, after planting but prior to flooding (pre-flood, post-emergence) or after emergence of the rice and flooding (post-flood, post-emergence) and may be applied to either direct seeded (drilled or surface seeded) or transplanted rice.

To be used in combination, it is not necessary that the two herbicides be applied in a physically combined form, or even at the same time. The combination effect results so long as the two herbicides are present on the foliage of the weeds at the same time in the rice crop, regardless of when they were applied. Thus, for instance a physical combination of the two herbicides could be applied, or one could be applied earlier than the other; however, the herbicides should be applied within 24 hours for better results.

Either herbicide could thus be applied in liquid or solid form, or a combination product containing both herbicides could be produced, again, in either liquid or solid form. Typical liquid formulations include emulsions, suspensions (including suspensions containing microcapsules), solutions, emulsifiable concentrates, and flowables. Solid products include forms such as granules, wettable powders, water-dispersible solid products (including water-dispersible granules containing microencapsulated pesticides) or dusts. Both types of compositions will generally contain, in addition to the active herbicides other ingredients such as solvents, wetting agents, suspending agents, anti-caking agents, dispersing agents, emulsifiers, antifreeze agents, antifoam agents, and other additives.

Either herbicide, or both, may be utilized in one of a number of known forms of controlled release compositions. Such compositions provide relatively slow or controlled release of the active ingredient into the environment and include, for example, encapsulations, microencapsulations, and various forms of controlled release liquid or granules.

Compositions according to this invention may contain the two herbicides in numerous different physical forms. In some cases, a composition may be produced by simply physically mixing ("tank mixing") commercially available products containing the active herbicides, for example, two emulsifiable concentrates containing the herbicides. Alternatively, a package may be manufactured and sold which contains overall the two herbicides in separate containers, but packaged together, commonly termed a "twin-pack".

Alternatively, previously prepared compositions ("premixes") containing the two herbicides can be produced. Typical liquid compositions would include an emulsifiable concentrate containing both herbicides, and a two-phase emulsion (or microemulsion) with one herbicide in each phase.

However, a similar solid product containing both herbicides could likewise be produced, for instance, as impregnated granules. Similarly, other solid formulations such as wettable powders or dusts could be prepared.

Again similarly, using appropriate ingredients and conditions, it would be possible to prepare microencapsulated products in which one or both herbicides are contained within a microcapsule and said microencapsulated products could be sold in either liquid form (i.e., capsule suspensions) or solid form (i.e., water-dispersible granules produced by drying of microcapsule suspensions). One type of liquid form would be a microcapsule suspension in which one of the herbicides is contained within the capsules while the other is present in a nonencapsulated form, in the continuous liquid phase. The types of formulations or compositions which may contain these two herbicides is not limited by those enumerated herein, as other types of formulations would likely be envisaged by those skilled in the art.

Additionally, other biocidically active ingredients or compositions may be combined with the herbicidal compositions of the present invention and used in the methods of the present invention. In addition, the synergistic active ingredients of the present invention can also include insecticides, fungicides, bactericides, acaracides, nematicides, plant growth regulators, fertilizers and plant nutrients, or other herbicides, especially herbicides known to be useful for controlling weeds in a rice crop. Common partner products added to propanil products to control grasses larger than six leaves and to control propanil resistant grasses include but are not limited to thiocarbamates (such as motinate and thiobencarb), chloroacetamides (such as butachlor) and auxins (such as quinclorac).

The control of weeds by the combination of the propanil based product and an amount of at least one ACCase inhibitor herbicide, is illustrated by the following examples:

EXAMPLE 1

In a small plot test in Arkansas a composition containing cyhalofop (formulated as Clincher® (cyhalofop) SF containing 2.38 pounds of active ingredient/gallon) when applied to a weedy rice plot at the high recommended rate of 15 fluid ounces/acre (0.279 pounds ai/acre) to control 2-3 leaf barnyard grass controlled the grasses but provided no (0%) control of the broadleaf weeds and sedges present at the time of application. While a composition containing propanil (formulated as Super Wham® (propanil) containing 4 pounds of active ingredient/gallon) plus cyhalofop (formulated as Clincher® (cyhalofop) SF containing 2.38 pounds of active ingredient/gallon) was applied as a tank mix to a weedy rice plot to control 2-3 leaf barnyard grass at 3 pounds propanil plus 0.070 pounds cyhalofop resulted in 100% control of all grasses, broadleaf weeds and sedges present at the time of application. Note that the label recommended rate for Clincher® (cyhalofop) SF for controlling grasses in the 2-3 leaf stage is 13.5 fluid ounces/acre (0.251 pounds cyhalofop/acre). The use of 0.07 pounds cyhalofop/acre in combination with 3 pounds of propanil is approximately 3.6 times less cyhalofop than the label recommended rate.

EXAMPLE 2

In a small plot test in Arkansas a composition containing fenoxaprop (formulated as Ricestar® (fenoxaprop-p-ethyl) containing 0.58 pounds of active ingredient/gallon) when applied to a weedy rice plot at the high recommended rate of 17 fluid ounces/acre (0.077 pounds ai/acre) to control 3-4 leaf barnyard grass controlled the grass species but provided no (0%) control of the broadleaf weeds and sedges present at the time of application. While a composition containing propanil (formulated as Super Wham® (propanil) containing 4 pounds of active ingredient/gallon) plus fenoxaprop (formulated as Ricestar® (fenoxaprop-p-ethyl) containing 0.58 pounds of active ingredient/gallon) was applied as a tank mix to a weedy rice plot to control 8-14 leaf barnyard grass at 6 pounds propanil plus 0.010 pounds fenoxaprop resulted in 100% control of all grasses, broadleaf weeds and sedges present at the time of application. Note that 6 pounds of propanil/acre alone would not be expected to control barnyard grass above 6 leaves and the highest label recommended rate for fenoxaprop controlling grasses at the 3 to 4 leaf stage is 17 fluid ounces product/acre (0.077 pounds active ingredient/acre). However, combining the high rate of propanil (6 pounds/acre) with fenoxaprop at 0.01 pounds/acre, or approximately 7.7 times below the highest recommend rate, provided complete control of the weeds present.

EXAMPLE 3

In a small plot test in Arkansas a composition containing propanil (formulated as Propanil 36 EC containing 3 pounds of active ingredient/gallon) plus fenoxaprop (formulated as Whip 360® (fenoxaprop-p-ethyl) containing 0.57 pounds of active ingredient/gallon) was applied as a tank mix to a weedy rice plot to control 4 leaf barnyard grass at 3 pounds propanil plus 0.009 pounds fenoxaprop. The results are shown in Table 2. Note that the label recommended rate for Whip 360® (fenoxaprop-p-ethyl) for controlling grasses in the 4 leaf stage is 12.8 fluid ounces/acre (0.057 pounds fenoxaprop/acre). The use of 0.009 pounds fenoxaprop/acre in combination with 3 pounds of propanil is approximately 6.3 times less fenoxaprop than the label recommended rate.

TABLE 3

| WEED GROUP | WEED | % CONTROL 5 DAA* | % CONTROL 22 DAA* |
|---|---|---|---|
| Grass | Barnyard grass | 98 | 90 |
| Grass | Broadleaf signalgrass | 94 | 91 |
| Sedge | Sedge | 100 | na |
| Broadleaf Weed | Hemp Sesbania | na | 100 |

DAA* = Days after Application

EXAMPLE 4

In a commercial field application by air in Arkansas a composition containing propanil (formulated as Super Wham® (propanil) containing 4 pounds of active ingredient/gallon) plus cyhalofop (formulated as Clincher® cyhalofop) SF containing 2.38 pounds of active ingredient/gallon) was applied as a tank mix to a weedy rice field to control 6 tiller barnyard grass at 5 pounds propanil plus 0.093 pounds cyhalofop resulted in 100% control of all grasses, broadleaf weeds and sedges present at time of application when evaluated 5 and 13 days after application. Note that 5 pounds of propanil/acre alone would not be expected to control even one tiller barnyard grass and the highest label recommended rate for cyhalofop controlling large grasses is 15 fluid ounces product/acre (0.278 pounds active ingredient/acre). The use of 0.093 pounds cyhalofop/acre in combination with 5 pounds of propanil is approximately 3 times less cyhalofop than the label recommended rate.

EXAMPLE 5

In a commercial field application by ground sprayer in California a composition containing propanil (formulated as Super Wham® (propanil) containing 4 pounds of active ingredient/gallon) plus cyhalofop (formulated as Clincher® (cyhalofop) SF containing 2.38 pounds of active ingredient/gallon) was applied as a tank mix to a weedy rice field to control 35 leaf Sprangletop (a grass species) at 6 pounds propanil plus 0.112 pounds cyhalofop resulted in 100% control of the Sprangletop present at the time of application. Note that propanil alone will not control Sprangletop and the recommended rate for cyhalofop to control Sprangletop is 13.5 to 15 fluid ounces product/acre (0.251 to 0.279 pounds active ingredient/acre) or approximately 2.2 to 2.5 times less cyhalofop than the label recommended rate.

EXAMPLE 6

In a small plot test in Mississippi a composition containing propanil (formulated as Super Wham® (propanil) containing 4 pounds of active ingredient/gallon) plus cyhalofop (formulated as Clincher® (cyhalofop) SF containing 2.38 pounds of active ingredient/gallon) was applied as a tank mix to a weedy rice plot to control large tillering grasses, broadleaf weeds and sedges at 4 pounds propanil plus 0.149 pounds cyhalofop and at 5 pounds propanil plus 0.093 pounds cyhalofop resulted in the control of all grasses, broadleaf weeds and sedges present at the time of application. Note that neither the 4 pound nor the 5 pound rates of propanil alone would be expected to control the weeds at the growth stage they were treated and that the highest labeled recommended rate of cyhalofop is 15 fluid ounces product/acre (0.278 pounds active ingredient/acre) would not control any of the broadleaf weeds or sedges while propanil in combinations with approximately 2 to 3 times less than the recommended rate of cyhalofop/acre provided weed control.

EXAMPLE 7

In a small plot test in Arkansas a composition containing propanil (formulated as Super Wham® (propanil) containing, 4 pounds of active ingredient/gallon) plus cyhalofop (formulated as Clincher® (cyhalofop) SF containing 2.38 pounds of active ingredient/gallon) was applied as a tank mix to a weedy rice plot to control 4 to 13 inch barnyard grass and 1 to 6 inch Sprangletop® (two grass species). The chemical rates in pounds/acre were:

TABLE 4

| PROPANIL/CYHALOFOP |
| --- |
| 5 pounds/0 pounds |
| 5 pounds/0.093 pounds |
| 5 pounds/0.130 pounds |
| 4 pounds/0 pounds |
| 4 pounds/0.074 pounds |
| 4 pounds/0.112 pounds |
| 3 pounds/0 pounds |
| 3 pounds/0.056 pounds |
| 3 pounds/0.093 pounds |
| 3 pounds/0.186 pounds |
| 0 pounds/0.279 pounds |

The following observations were made 12 days after application. All rates of propanil applied showed excellent broadleaf and sedge control. When applied alone, all rates of propanil showed expected lack of Sprangletop control. The treatment of 3 pounds propanil combined with 0.186 pounds cyhalofop showed weak grass control that may be attributed to antagonism. The high labeled rate for cyhalofop (0.279 pounds/acre) showed excellent grass control and an expected weakness in controlling broadleaf weeds and sedges. The combination rates of propanil and cyhalofop other than the 3 pounds propanil combined with 0.186 pounds cyhalofop showed, broad spectrum weed control of grasses, broadleaf weeds and sedges 12 days after application.

EXAMPLE 8

In a. commercial field application by air in Arkansas a composition containing propanil (formulated as Super Wham® (propanil) containing 4 pounds of active ingredient/gallon) plus cyhalofop (formulated. as Clincher® cyhalofop) SF containing 2.38 pounds of active ingredient/gallon) was applied as a tank mix to half a weedy rice field to control up to tillering barnyard grass at 4 pounds propanil plus 0.037 pounds cyhalofop resulted in 100% control of all grasses, broadleaf weeds and sedges present at time of application when evaluated 7 days after application. The other half of the weedy rice field was treated with a. composition containing only propanil (formulated as Super Wham® (propanil) containing 4 pounds of active ingredient/gallon) at 4 pounds propanil resulting in poor barnyard grass control 7 days after application. Note that 4 pounds of propanil/acre alone would not be expected to control even one tiller barnyard grass and the label recommended rate for cyhalofop controlling large grasses is 15 fluid ounces product/acre (0.279 pounds active ingredient/acre) or approximately 7.5 times more cyhalofop than was combined with the propanil.

EXAMPLE 9

In a commercial field application by air in Arkansas a composition containing propanil (formulated as Super Wham® (propanil) containing 4 pounds of active ingredient/gallon) plus cyhalofop (formulated as Clincher® (cyhalofop) SE containing 2.38 pounds of active ingredient/gallon) was applied as a tank mix to a weedy rice field to control up to tillering barnyard grass at 5 pounds propanil plus 0.093 pounds cyhalofop resulted in 100% control of all grasses, broadleaf weeds and sedges present at time of application when evaluated 7 days after application. Note that 5 pounds of propanil/acre alone would not be expected to control even one tiller barnyard grass and the label recommended rate for cyhalofop controlling large grasses is 15 fluid ounces product/acre (0.279 pounds active ingredient/acre), a rate approximately 3 times greater than that combined with propanil.

EXAMPLE 10 in a commercial field application by air in Arkansas a composition containing propanil (formulated as Super Wham® (propanil) containing 4 pounds of active ingredient/gallon) plus cyhalofop (formulated as Whip 360® (fenoxaprop-p-ethyl) containing 0.57 pounds of active ingredient/gallon) was applied as a tank mix to a weedy rice field to control barnyard grass, broadleaf weeds and sedges. The weedy rice field was divided into three sections. One section of the weedy rice field was treated only with Super Wham® (propanil) at a rate of 4 pounds of active ingredient (propanil) per acre. A second section of the weedy rice field was treated with Super Wham® (propanil) at a rate of 3 pounds active ingredient (propanil) plus Whip (fenoxaprop-p-ethyl) at a rate of 0.012 pounds active ingredient (fenoxaprop) per acre. The third section of the weedy rice field was treated with Super Wham® (propanil) at a rate of 2.5 pounds active ingredient (propanil) plus Whip® (fenoxaprop-p-ethyl) at a rate of 0.010 pounds active ingredient (fenoxaprop) per acre. In this demonstration the lower rate of propanil plus fenoxaprop, at a. rate approximately 7 times lower than the highest recommended rate/acre, provided similar or better biological activity than the 4 pound per acre rate of propanil alone at 3 and 7 days alter application in controlling barnyard grass and broadleaf weeds present (indigo, morningglory, tea weed, and Ameranthus).

EXAMPLE 11

In a commercial field, application by air in Arkansas a composition containing propanil (formulated. as Super Wham® (propanil) containing 4 pounds of active ingredient/gallon) plus cyhalofop (formulated as Whip 360® (fenoxaprop-p-ethyl) containing 0.57 pounds of active ingredient/gallon) was applied to a weedy rice field to control grass (crab grass) and a broadleaf weed (morningglory). The field was divided into two sections. One section of the rice field was treated only with Super Wham® (propanil) at a rate of 4 pounds of active ingredient (propanil) per acre. A second section of the rice field was treated with Super Wham (propanil) at a rate of 3.5 pounds active ingredient (propanil) plus Whip (fenoxaprop-p-ethyl) at a rate of 0.013 pounds fenoxaprop/acre (a rate of fenoxaprop approximately 5.5 times less than the recommended rate/acre). In this demonstration the combination of propanil plus fenoxaprop provided similar or better biological activity than the 4 pound per acre rate of propanil alone at 4 and 8 days after application in controlling both the crab grass and morningglory.

EXAMPLE 12

In a small plot test in Colombia a composition, containing propanil (formulated as an emulsifiable concentrate containing 480 grams of active ingredient/liter) plus fenoxaprop (formulated as Furore containing 45 grams active ingredient/liter) was applied to rice to control germinating to tillering grasses, germinating to 2-3 leaf broadleaf weeds and germinating to 2-5 leaf sedges. In this test propanil was applied at rates of 3.36, 3.00, and 2.75 kg active ingredient alone and in combinations with fenoxaprop at rates of 0.85, 0.30, 0.20, 0.10 and 0.05 kg active ingredient per hectare. The fenoxaprop rates listed above were also applied alone, without propanil. In this test the combinations of propanil at 3.36, 3.00 and 2.75 kg plus fenoxaprop at 0.10 kg per hectare provided superior control of grasses (*Echinochloa coloman*, *Eleusine indica*, and *Digitaria sanguinalis*), broadleaf weeds (*Cassia tora* and *Ammonia coccinea*) and sedge (*Cyperus rotundas*) than any propanil or fenoxaprop rate alone.

EXAMPLE 13

Based on the results of Example 10, in a second small plot test in Colombia a composition containing propanil (formulated as an emulsifiable concentrate containing 480 grams of active ingredient/liter and as a wetable granule containing 800 grams of active ingredient/kg) plus fenoxaprop (formulated as Furore containing 45 grams active ingredient/liter) was applied to rice to control grasses, leaf broadleaf weeds and leaf sedges. In this test, the treatments were made at two different timings. The grasses (*Echinochloa colonum*, *Ischaemum rugosum*, *Rottboellia cochinchinensis*, and *Digitaria sanguinalis*) were in the 1 to 3 leaf stage for the first timing and in the 4 leaf to 1 tiller stage for the second timing. The broadleaf weeds (*Ipomeoa sp.*, *Jussiaea linifolia* and *Ammania coccinea*) were between the 2 to 4 leaf stage for the first timing and more than 4 leaf stage for the second timing. The sedges (*Fimbristilis annua* and *Cyprus feraz*) were in the 2 to 5 leaf stage for the first timing and more than 5 leaf stage for the second timing). In this test the propanil formulations were evaluated at 3.6, 2.7, 1.8, and 0.9 kg active ingredient/hectare alone and in combination with 0.01, 0.0075, 0.005 and 0.0025 kg fenoxaprop/hectare respectively. The propanil+fenoxaprop combination rates of 3.6+0.01 and 2.7+0.0075 kg/hectare gave superior weed control, particularly evident at the second timing on larger more difficult to control weeds, than the propanil treatments alone.

EXAMPLE 14

In a small plot test in Colombia a composition containing propanil (formulated as an emulsifiable concentrate containing 480 grams of active ingredient/liter) plus cyhalofop (formulated as Clincher® (cyhalofop) containing 180 grams active ingredient/liter) was applied to rice to control grasses, leaf broadleaf weeds and leaf sedges. In this test, the treatments were made at two different timings. The grasses (*Echinochloa colonum*, *Ischaemum rugosum*, *Rottboellia cochinchinensis*, and *Digitaria sanguinalis*) were in the 1 to 3 leaf stage for the first timing and in the 4 leaf to 1 tiller stage for the second timing. The broadleaf weeds (*Iporneoa sp.*, *Jussiaea linifolia* and *Ammonia coccinea*) were between the 2 to 4 leaf stage for the first timing and more than 4 leaf stages for the second timing. The sedges (*Fimbristilis annua* and *Cyprus feraz*) were in the 2 to 5 leaf stage for the first timing and more than 5 leaf stage for the second timing). A series of propanil rates (0.840. 1.12. 1.40, 1.68, 2.24, 2.52, 2.80, 3.36, 4.20, 4.48, and 5.60 kg active ingredient/hectare) were combined with cyhalofop at a constant ratio of 0.0186 kg cyhalofop/hectare for every 1 kg propanil/hectare (0.0156, 0.0208, 0.0261 0.0313, 0.0417, 0.0469, 0.0521, 0.0625, 0.0782, 0.0834, and 0.1042 kg cyhalofop/hectare respectively). The propanil +cyhalofop combination rates at 2.52+0.0469 kg/hectare and above gave weed control, particularly evident at the second timing on larger more difficult to control weeds, than the lowest commonly recommended propanil rate (3.36 kg/hectare) alone (see example 11 for weed control with propanil alone that was conducted at the same time and location as this test).

Although the present invention has been described and illustrated with respect to preferred embodiments and a preferred user thereof, it is not to be so limited since modifications and changes can be made therein which are within the full scope of the invention.

I claim

1. A method to control weeds while cultivating rice in a field, comprising the step of:
    applying a synergistic composition comprising as an active ingredient an herbicidal compound:
    said herbicidal compound comprising an herbicidally effective amount of a propanil based herbicide mixed with at least one ACCase inhibitor herbicide wherein the weight ratio of the herbicidal compound ranges from about 1 lbs of said propanil based herbicide to about 0.0018 to 0.04 lbs of said at least one ACCase inhibitor per acre to said field, wherein said at least one ACCase inhibitor is selected from the group consisting of cyhalofop and fenoxaprop to control weeds while cultivating rice in a field.

2. The method of claim 1 wherein said synergistic composition comprises as an active ingredient an effective amount of a compound selected from the group consisting of insecticide, fungicide, bactericide, acaracide, nematicide, plant growth regulator, fertilizer, and plant nutrients.

3. The method of claim 1 wherein said at least one ACCase inhibitor is cyhalofop wherein the weight ratio of the herbicidal compound ranges from about 1 lbs. of said propanil based herbicide to about 0.009 to about 0.04 lbs. of said cyhalofop per acre.

4. A method to reduce the amount of propanil required to control weeds in a rice field which comprises applying to said weeds:
    (a) propanil mixed with;
    (b) cyhalofop
    wherein component (b) is applied at an effective rate such that it overcomes or reduces the antagonistic interaction between components (a) and (b) and effectively reduces the amount of propanil required to achieve the same level of control by twenty percent.

5. The method of claim 1 wherein said weeds are sedge weeds.

* * * * *